United States Patent
Kidambi et al.

(10) Patent No.: US 12,050,218 B2
(45) Date of Patent: Jul. 30, 2024

(54) MITOCHONDRIAL PROTEASE OMA1 AS A MARKER FOR BREAST CANCER

(71) Applicant: NUtech Ventures, Lincoln, NE (US)

(72) Inventors: Srivatsan Kidambi, Lincoln, NE (US); Oleh Khalimonchuk, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 497 days.

(21) Appl. No.: 16/476,961

(22) PCT Filed: Jan. 12, 2018

(86) PCT No.: PCT/US2018/013497
§ 371 (c)(1),
(2) Date: Jul. 10, 2019

(87) PCT Pub. No.: WO2018/132662
PCT Pub. Date: Jul. 19, 2018

(65) Prior Publication Data
US 2019/0369100 A1    Dec. 5, 2019

Related U.S. Application Data

(60) Provisional application No. 62/446,434, filed on Jan. 14, 2017.

(51) Int. Cl.
| | | |
|---|---|---|
| G01N 31/00 | (2006.01) | |
| C07K 16/30 | (2006.01) | |
| C12N 9/64 | (2006.01) | |
| G01N 33/53 | (2006.01) | |
| G01N 33/574 | (2006.01) | |

(52) U.S. Cl.
CPC ... *G01N 33/57415* (2013.01); *C07K 16/3015* (2013.01); *C12N 9/6489* (2013.01); *G01N 33/57484* (2013.01); *G01N 2333/8146* (2013.01)

(58) Field of Classification Search
None
See application file for complete search history.

(56) References Cited

U.S. PATENT DOCUMENTS 5,169,774 A * 12/1992 Frankel .............. C07K 16/3015
                                                    530/808
2018/0371007 A1 * 12/2018 Moghadam .......... C12Q 1/6883

FOREIGN PATENT DOCUMENTS

| WO | 2005118834 A2 | 12/2005 | |
| WO | WO-2005118834 A2 * | 12/2005 | ........... C12Q 1/6886 |

OTHER PUBLICATIONS https://Awww.ncebi.nim.nih.gov/pmc//articles/PMC3293553/ (Year: 2012).*
https:/Awww.ncbi.nim.nih.gov/omc/articles/PMC5627902/ (Year: 2017).*
https:/Avww.ncbi.nim.nih.gov/pme/articles/PMC5748994/ (Year: 2018).*
https://media.cellsignal.com/coa/95473/1/95473-Iot-1-coa.pdf (Year: 2017).*
Bohovych et al., Stress-triggered Activation of the Metalloprotease Oma1 Involves Its C-Terminal Region and is Important for Mitochondrial Stress Protection in Yeast; The Journal of Biological Chemistry, 2014, vol. 289, No. 19, pp. 13259-13272.
Khalimonchuk et al., OMA1 as a Theranostic Marker for Breast Cancer; 2017, 2-pages.
Zhang et al., Membrane depolarization activates the mitochondrial protease OMA1 by stimulating self-cleavage; EMBO report, 2013, vol. 15, No. 5, pp. 576-586.

* cited by examiner

*Primary Examiner* — Lisa V Cook
(74) *Attorney, Agent, or Firm* — Jeannie M. Boettler; Sandberg Phoenix & von Gontard, PC

(57) ABSTRACT

The use of mitochondrial protease OMA1 as a theranostic marker for breast cancer, tumor progression, metastatis and drug responsiveness is disclosed herein.

10 Claims, 18 Drawing Sheets

MITOCHONDRIAL PROTEASE OMA1 AS A MARKER FOR BREAST CANCER

CROSS REFERENCE TO RELATED APPLICATION

This application is a national phase application of International Application No. PCT/US2018/013497 (published as WO 2018/132662), filed Jan. 12, 2018, which claims benefit to U.S. Provisional Patent Application No. 62/446,434, filed on Jan. 14, 2017, both of which are hereby incorporated by reference in their entireties.

BACKGROUND OF THE DISCLOSURE

The present disclosure relates generally to the use of mitochondrial protease OMA1 as a theranostic marker for breast cancer, tumor progression, metastatis and drug responsiveness. Particularly, it has been found herein that impaired mitochondrial protein quality control (MQC) function through OMA1 deficit can drive malignancy and metastatic progression in breast cancer.

Breast cancer is a complex disease affecting over 180,000 women annually involving a continuously changing phenotype and microenvironment leading to differences in the gene and protein profile of the neoplasm. Metastasis to vital organs including lungs, liver, bone, and brain is a major cause for breast cancer-related deaths. Two main processes, migration and invasion, mediate the metastatic activity of tumor cells. Mounting evidence indicates that altered mitochondrial functions play a significant role(s) in the regulation of tumor cell biology and are likely involved in tumor progression including metastasis. Growing evidence indicates that mitochondrial integrity is central to cancer cell physiology, particularly with regard to energy production and cell survival in highly dynamic tumor environments. Perturbations to mitochondrial integrity by mutations or functional decline lead to mitochondrial dysfunction, potentially impacting metastatic properties of neoplastic cells. Many cancer cells undergo the metabolic adaptation known as aerobic glycolysis, or Warburg effect, which involves enhanced utilization of glucose or pyruvate for anabolic processes underpinning rapid proliferation. These cells also rely on glutamate anaplerosis to replenish the tricarboxylic acid (TCA) cycle with pyruvate. Alterations in mitochondrial function and the subsequent metabolic reprogramming are now being recognized as important hallmarks of malignancy and metastasis. To date, several studies report a loss of mitochondrial function in various cancers, including breast cancer. However, the mechanisms by which mitochondrial malfunction contributes to cancer progression remain far from clear.

Mitochondria are highly dynamic organelles whose form and shape are regulated through two critical processes: fission and fusion. The dynamic nature of mitochondrial networks allows the adjustment of mitochondrial morphology and metabolism to specific cellular processes and is also essential for mitochondrial protein quality control (MQC). MQC comprises a unique and conserved set of interrelated mechanisms critical for the organelle's health. Recent reports implicate several MQC modules in development and progression of various cancers. For instance, elevated activities of ATP-driven proteases Lon Peptidase 1 (LONP) and Caseinolytic Mitochondrial Matrix Peptidase Chaperone Subunit (CLPXP) have been shown to correlate with tumor development and progression. Reciprocally, downregulation of these proteases has been proposed as a potential therapeutic strategy in patients with lymphoma and acute myeloid leukemia, respectively. Activities of several other MQC proteases have been suggested to prevent malignant progression; however, the molecular details of this process remain to be clarified.

Accordingly, there is a need in the art to identify and utilize next generation diagnostic and therapeutic targets that underlie mitochondrial dysfunction. This approach could potentially allow for early detection and clinical management of cancer, and particularly, breast cancer.

BRIEF DESCRIPTION OF THE DISCLOSURE

The present disclosure is generally related to the use of OMA1, a mitochondrial metalloprotease, as a theranostic biomarker of cancer, and in particular, breast cancer. Particularly, mitochondrial integrity is central to key tumor cell response such as energy production and cell survival when exposed to a dynamically modulating environment. Accordingly, the use of OMA1 as a biomarker and therapeutic target, now found to underlie mitochondrial dysfunction, for prognosis of a tumor's metastatic behavior and clinical intervention has huge implications in introducing a new player in the medical arena.

Accordingly, in one aspect, the present disclosure is directed to a method of diagnosing metastatic breast cancer in a subject in need thereof, the method comprising: measuring an expression level of protein OMA1 Zinc Metallopeptidase (OMA1) in a sample obtained from the subject; and comparing the expression level of protein OMA1 in the sample with a protein OMA1 reference expression level, wherein the expression level of protein OMA1 in the sample less than the protein OMA1 reference expression level indicates metastatic breast cancer.

In another aspect, the present disclosure is directed to a method of monitoring effectiveness of a therapy in a subject having or suspected of having a metastatic breast cancer, the method comprising: measuring an expression level of protein OMA1 Zinc Metallopeptidase (OMA1) in at least a first chronological sample obtained from the subject; administering the therapy; measuring an expression level of protein OMA1 Zinc Metallopeptidase (OMA1) in at least a second chronological sample obtained from the subject, analyzing the expression level of protein OMA1 Zinc Metallopeptidase (OMA1) in at least the first chronological sample and the expression level of protein OMA1 Zinc Metallopeptidase (OMA1) in at least the second chronological sample, wherein an increase in the expression level of protein OMA1 Zinc Metallopeptidase (OMA1) in the second chronological sample as compared to the expression level of protein OMA1 Zinc Metallopeptidase (OMA1) in a first chronological sample indicates effectiveness of the therapy.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 1A depicts extracellular acidification rates (ECAR) in wild type and oma1$^{-/-}$ mouse embryonic fibroblasts under basal, FCCP-stimulated, and glycolysis-ablating (2-DG) conditions. Cells were cultured in the media containing 10 mM glucose. Data are shown as mean values of 3 independent experiments±S.E.M.; p<0.01, by unpaired t-test. FIG. 1B depicts growth rate of wild type (WT) and oma1$^{-/-}$ MEF cells under conditions of glutamate pathway inhibition by BPTES. Cells were cultured in the 10 mM galactose-containing medium with (left panel) or without (right panel) 10 μM BPTES for the indicated periods of time and the number of viable cells at each time point has been assessed. Data represent the mean±S.D. (n=3 biological replicates); p<0.01, by unpaired t-test. FIG. 1C are live phase contrast images of MEF WT and oma1$^{-/-}$ cells at 2 days after seeding in normal culture conditions and after overgrowth for 7 days at 100% confluence. Unlike the WT cells, post-quiescent oma1$^{-/-}$ MEFs exhibited characteristic lamellopodia-like structures (white arrows) after overgrowth. FIG. 1D depicts the prevalence of cells with protrusions was analyzed in WT and oma1$^{-/-}$ MEF cells two days after re-seeding on 6-well plates after one week of growth at 100% confluence. Each well was randomly imaged in 2-3 fields of view, each containing 15-50 cells. Of the cells in the field of view, the number of cells with long lamellopodia and cells with normal lamellopodia were counted. The data was plotted as a scatter plot where each point represents percentage of cells with long lamellopodia of total cells in one field of view. Data was plotted as a scatter plot where each point represents protrusion size in one cell, weighted average is represented as a horizontal line. FIG. 1E depicts proliferation of MEF WT and oma1$^{-/-}$ cells seeded after overgrowth of 7 days at 100% confluence. Data represent the mean±S.D. of n=3 biological replicates; **p<0.01. FIG. 1F depicts paraformaldehyde-fixed WT and oma1$^{-/-}$ MEF cells on 2nd day after seeding post-overgrowth of 7 days at 100% confluence. Samples were co-stained for Actin with Alexa Fluor 488-conjugated phalloidin (and Hoechst to visualize nuclei) and imaged by confocal microscopy. The arrows mark rearranged actin patches. Scale bar, 20 μm.

FIG. 2A at the top panel shows a representative western blot of extracts from the metastatic pleural effusion mammary tumor 21MT-1 cells after stable transfection with an shRNA scrambled control, and shRNA directed against OMA1. Steady-state levels of the protease were detected by immunoblotting with anti-OMA1. The tubulin served as a loading control and was visualized with the respective antibody. The bottom panel shows quantitative assessment of the above immunoblots. The error bars indicate mean data±S.D. n=3 independent experiments; ***p<0.001 by unpaired t-test. FIG. 2B is a representative western blot of extracts from the non-tumorigenic MCF10A cells after transfection with an shRNA scrambled control, and shRNA directed against OMA1. Steady-state levels of the protease were detected by immunoblotting with anti-OMA1. The tubulin served as a loading control and was visualized with the respective antibody. FIG. 2C depicts live phase contrast and fluorescent images of control and OMA1 knockdown (KD) 21MT-1 cells at 24 hours and 48 hours after seeding in normal culture conditions. Unlike the control cells, OMA1 KD cells exhibit characteristic lamellopodia-like structures (white arrows) after overgrowth. Control and OMA1 KD 21MT1 cells were stained for Actin with Alexa Fluor 488-conjugated phalloidin and Nuclei with Hoeschst imaged by confocal microscopy actin. The arrows indicate lamellopodia. Scale bar, 20 μm. FIG. 2D depicts the prevalence of cells with protrusions was analyzed in WT and OMA1 KD 21MT-1 cells after two days of growth. Each well was randomly imaged in 3-4 fields of view, each containing 40-75 cells. Of the cells in the field of view, the number of cells with long lamellopodia and cells with normal lamellopodia were counted. The data was plotted as a scatter plot where each point represents percentage of cells with long lamellopodia of total cells in one field of view. Data was plotted as a scatter plot where each point represents protrusion size in one cell, weighted average is represented as a horizontal line. FIG. 2E shows the size of protrusions analyzed in control and OMA1 KD 21MT-1 cells after two days of growth. Each well was randomly imaged in 3-4 fields of view, each containing 40-75 cells. Of the cells in the field of view, the number of cells with long lamellopodia and cells with normal lamellopodia were counted. The data was plotted as a scatter plot where each point represents percentage of cells with long lamellopodia of total cells in one field of view. Data was plotted as a scatter plot where each point represents protrusion size in one cell; weighted average is represented as a horizontal line. FIG. 2F show live phase contrast images of control and OMA1 KD MCF10A cells at 24 hours and 48 hours after seeding in normal culture conditions. Unlike the cancer cells, MCF10A OMA1 KD cells did not exhibit characteristic lamellopodia-like structures. Scale bar, 20 μm. FIG. 2G depicts proliferation of 21MT-1 WT and OMA1 KD cells seeded after overgrowth of 7 days at 100% confluence. Data represent the mean±S.D. of n=3 biological replicates; *p<0.05, ***p<0.001. FIG. 2H depicts proliferation of MCF10A WT and OMA1 KD cells seeded after overgrowth of 7 days at 100% confluence. Data represent the mean±S.D. of n=3 biological replicates.

FIG. 3A depicts a representative oxygen consumption rate (OCR) graph in control and OMA1-depleted 21MT-1 cells under basal, oligomycin A (OLA), FCCP, and Antimycin A/Rotenone (AA+Rot.) stimulated conditions. Cells were cultured in the medium containing 10 mM galactose. FIG. 3B depicts respiratory control ratios in control and OMA1 KD 21MT-1 cells cultured in 10 mM galactose medium. Data represent the mean±S.E.M. (n=3 biological replicates); *p<0.05, by t-test. FIG. 3C depicts the growth rate of control and OMA1-depleted 21MT-1 cells under conditions of glutamate pathway inhibition. Cells were cultured in the 10 mM galactose-containing medium in the presence of 10 μM BPTES for the indicated periods of time and the number of viable cells at each time point has been assessed. Data represent the mean±S.D. (n=3 biological replicates); *p<0.05, ***p<0.001, by unpaired t-test.

FIG. 3D depicts visualization of mitochondria in living control and OMA1 KD 21MT-1 cells. Image of MitoTrackerR Red CMXRos-stained mitochondria in each respective cell type were captured using confocal microscopy, Scale bar, 5 μm. FIG. 3E are confocal images of immunostained actin fibers in paraformaldehyde-fixed control and OMA1 KD 21MT-1 cells show actin branching in the OMA1 depleted cancer cells, Scale bar, 5 μm.

FIG. 4A is fluorescent images showing BrdU and Ki67 staining in MCF10A, OMA1 KD MCFA10A, 21MT-1, and OMA1 KD 2MT-1 cells. Anti-BrdU visualized with Alexa Fluor 488-coupled secondary IgG (red); nucleus visualized with DAPI staining (blue); Scale bar, 200 μm. FIG. 4B includes bar diagrams showing no changes in BrdU positive cells in control and OMA1 KD cells in MCF10A cells after 2 days in culture (left diagram) and Ki67 staining for the MCF10A cells (right diagram). At least three independent experiments were conducted for each respective analysis. FIG. 4C is a bar diagram showing increase in Ki67 expression in OMA1 KD 21MT-1 cells compared to control cells after 2 days in culture. There was no significant difference in Ki67 expression in OMA1 KD and control MCF10A cells. At least three independent experiments were conducted for each analysis. FIG. 4D depicts migration assay data detailing the migration of cells out from a confluent monolayer onto a featureless scratch or wound. Representative phase images of control and OMA1 KD 21MT-1 cells at 24 hours and 48 hours. Scale bar, 20 μm. FIG. 4E depicts quantitative analysis of migratory properties of control and shOMA1 21MT-1 cells. The extent of wound closure was calculated as follows: % Wound Closure=[(Area at 0 h−Area at 24 or 48 h)/Area at 0 h]×100%. Bars show mean data±S.D. of 3 biological replicates; p<0.01, *p<0.001 by unpaired t-test. FIG. 4F depicts migratory properties of control and OMA1 KD MCF10A cells as analyzed in FIG. 4E.

FIG. 5A depicts qRT-PCR analysis of the expression of EMT marker genes in control and OMA1 KD 21MT-1 cells after 2 days in culture. The expression levels were normalized to GAPDH and to control cells. Data is presented as mean±S.D. from 3 biological replicates. *p<0.05; p<0.01; *p<0.001 by Student's t-test. FIG. 5B at the left panel includes immunoblots showing protein expression of specific EMT markers in control and OMA1 KD 21MT-1 cells. The right panel depicts densitometry analysis of the respective bands normalized after loading control (GAPDH) correction. Control cells grown served as control. Data are mean±S.D.; n=3 independent experiments; *p<0.05; p<0.01; *p<0.001 by Student's t-test.

FIGS. 6A-6C depict qRT-PCR analysis showing increased expression of canonical UPRmt genes AFG3L2 (FIG. 6A), CLPP (FIG. 6B), and HSPD1 (FIG. 6C) in control and OMA1-depleted 21MT-1 cells. n=3 independent experiments. Error bars show mean values±S.E.M.; p<0.01, by Student's t-test. FIGS. 6D & 6E are representative immunoblots of extracts from control and shOMA1 21MT-1 cells. Steady-state levels of the AFG3L2 (FIG. 6D) and HSPD1 (FIG. 6E) were detected with the respective antibodies. The tubulin served as a loading control and was visualized with the respective antibody. The bottom graphs show quantitative assessment of the western blots. Error bars, mean±S.E.M.; n.s., non-significant; p<0.01, by Student's t-test. FIG. 6F depicts representative flow cytometry analysis histograms of control and OMA1-depleted 21MT-1 cells, indicating lower mitochondrial membrane potential of OMA1 KD 21MT-1 cells. Cells were incubated with 50 nM TMRM under basal, and CCCP-induced uncoupling conditions. 50,000 cells were assayed for TMRM fluorescence in each experiment.

DETAILED DESCRIPTION

Figure 1A:
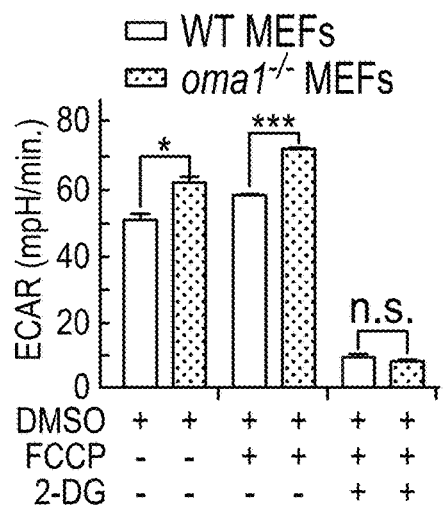
FIGS. 1A-1F shows that loss of OMA1 alters metabolic and proliferative properties of mouse embryonic fibroblasts.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

A. Definitions

As used herein, the term "sample" refers to a composition that is obtained or derived from a subject of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized. A "tissue" or "cell sample" refers to a collection of similar cells obtained from a tissue of a subject or patient. The source of the tissue or cell sample may be blood or any blood constituents (e.g., whole blood, plasma, serum) from the subject. The tissue sample can also be primary or cultured cells or cell lines. Optionally, the tissue or cell sample is obtained from a disease tissue/organ. The tissue sample can contain compounds which are not naturally intermixed with the tissue in nature such as preservatives, anticoagulants, buffers, fixatives, nutrients, antibiotics, and the like.

As used herein, the terms "control", "control cohort", "reference sample", "reference cell", "reference tissue", "control sample", "control cell", and "control tissue" refer to a sample, cell or tissue obtained from a source that is known, or believed, to not be afflicted with the disease or condition for which a method or composition of the present disclosure is being used to identify and/or treat. The control can include one control or multiple controls. In one embodiment, a reference sample, reference cell, reference tissue, control sample, control cell, or control tissue is obtained from a healthy part of the body of the same subject or patient in whom a disease or condition is being identified/treated using a composition or method of the present disclosure. In one embodiment, a reference sample, reference cell, reference tissue, control sample, control cell, or control tissue is obtained from a healthy part of the body of an individual who is not the subject or patient in whom a disease or condition is being identified/treated using a composition or method of the invention.

As used herein, "a subject in need thereof" refers to a subject or patient having, susceptible to or at risk of a specified disease, disorder, or condition. More particularly, in the present disclosure the methods of screening biomarkers is to be used with a subset of subjects who have, are susceptible to or are at an elevated risk for experiencing breast cancer, and in particular, metastatic breast cancer. Such subjects can be susceptible to or at elevated risk for breast cancer due to family history, age, environment, and/or lifestyle.

Based on the foregoing, because some of the method embodiments of the present disclosure are directed to specific subsets or subclasses of identified subjects (that is, the subset or subclass of subjects "in need" of assistance in addressing one or more specific conditions noted herein), not all subjects will fall within the subset or subclass of subjects as described herein for certain diseases, disorders or conditions.

As used herein, "susceptible" and "at risk" refer to having little resistance to a certain disease, disorder or condition, including being genetically predisposed, having a family history of, and/or having symptoms of the disease, disorder or condition.

As used herein, "diagnosing" and "diagnosis" are used according to their ordinary meaning as understood by those skilled in the art to refer to identifying that a subject is likely to develop or is at risk for developing breast cancer and/or identifying a subject with breast cancer, wherein the tumors are likely to progress including metastasis and/or increased tumor growth.

As used herein, the term "biomarker" refers to a molecule to be used for analyzing a subject's test sample. Examples of such biomarkers can be nucleic acids (such as, for example, a gene, DNA and RNA), proteins and polypeptides. In particularly preferred embodiments, the biomarker can be OMA1 Zinc Metallopeptidase (OMA1). A "theranostic biomarker" as used herein, refers to a single agent that allows for diagnosis, drug delivery and treatment response monitoring. More particularly, OMA1 is used herein to diagnose breast cancer, and in particular, metastatic breast cancer, in a subject, provide treatment to reduce tumor growth and/or metastasis in a subject having metastatic breast cancer, and monitor a subject undergoing treatment for metastatic breast cancer.

As used herein, "expression level of a biomarker" refers to the process by which a gene product is synthesized from a gene encoding the biomarker as known by those skilled in the art. The gene product can be, for example, RNA (ribonucleic acid) and protein. Expression level can be quantitatively measured by methods known by those skilled in the art such as, for example, northern blotting, amplification, polymerase chain reaction, microarray analysis, tag-based technologies (e.g., serial analysis of gene expression and next generation sequencing such as whole transcriptome shotgun sequencing or RNA-Seq), Western blotting, immunoassay procedure (e.g., enzyme-linked immunoassay (ELISA); sandwich assay format) and combinations thereof.

As used herein, "a reference expression level of a biomarker" refers to the expression level of a biomarker established for a subject without metastatic breast cancer, expression level of a biomarker in a normal/healthy subject without metastatic breast cancer as determined by one skilled in the art using established methods as described herein, and/or a known expression level of a biomarker obtained from literature. The reference expression level of the biomarker can also refer to the expression level of the biomarker established for any combination of subjects such as a subject without metastatic breast cancer, expression level of the biomarker in a normal/healthy subject without metastatic breast cancer, and expression level of the biomarker for a subject without metastatic breast cancer at the time the sample is obtained from the subject, but who later exhibits with metastatic breast cancer. The reference expression level of the biomarker can also refer to the expression level of the biomarker obtained from the subject to which the method is applied. As such, the change within a subject from visit to visit can indicate an increased or decreased risk for metastatic breast cancer. For example, a plurality of expression levels of a biomarker can be obtained from a plurality of samples obtained from the same subject and used to identify differences between the pluralities of expression levels in each sample. Thus, in some embodiments, two or more samples obtained from the same subject can provide an expression level(s) of a blood biomarker and a reference expression level(s) of the blood biomarker.

OMA1 Zinc Metallopeptidase (OMA1) is a conserved metallopeptidase that has recently emerged as a critical regulator of metabolic homeostasis, mitophagy, and apoptosis. At least in part, such functional versatility is attributed to the enzyme's ability to process the GTPase, OPA1, and thus rapidly modulate the mitochondrial network. Recently, it was discovered that OMA1-deficient mouse embryonic fibroblasts exhibit increased aerobic glycolysis upon culturing conditions that require maximal bioenergetic output. Intriguingly, results of the Human Protein Atlas Consortium initiative report that OMA1 protein levels are extremely low in breast and testicular cancer tissues, as well as in lymphomas, thereby indicating that the protease may be inactivated in these cancers. However, whether OMA1 plays a role in development and progression of breast adenocarcinoma is unknown.

It has now been found that depletion of OMA1 in stable, patient-derived breast cancer cells isolated from the metastatic pleural effusion increased expression of the canonical mitochondrial unfolded protein response (UPRmt) markers, cell spreading, and lamellopodia formation. Moreover, sustained silencing of OMA1 resulted in more cells exhibiting mesenchyme-like morphology, reduced proliferation, and enhanced migratory properties indicative of the epithelial-mesenchyme transition (EMT). Consistent with enhanced metastatic abilities of the OMA1-depleted breast cancer cells, a significant upregulation of mesenchymal markers and decreased expression of epithelial markers was observed at both the gene and protein levels. Based on these findings, it is now believed that impaired MQC function through OMA1 deficit can drive malignancy and metastatic progression in breast cancer.

Accordingly, in one embodiment, the present disclosure is generally directed to methods of diagnosing metastatic breast cancer in a subject in need thereof. The methods include: measuring an expression level of protein OMA1 Zinc Metallopeptidase (OMA1) in a sample obtained from the subject; and comparing the expression level of protein OMA1 in the sample with a protein OMA1 reference expression level, wherein the expression level of protein OMA1 in the sample is less than the protein OMA1 reference expression level indicates metastatic breast cancer.

Generally, the subject is a mammal (e.g., human, non-human primate, rat, mouse, cow, horse, pig, sheep, goat, dog, cat, etc.). The subject can be a clinical patient, a clinical trial volunteer, a companion animal, an experimental animal, etc. The subject can be suspected of having or at risk for having a condition (such as metastatic prostate cancer) or be diagnosed with a condition (such as metastatic prostate cancer). According to one embodiment, the subject to be treated according to this invention is a human.

Suitable samples can be, for example, saliva, whole blood, plasma, serum and a cheek swab. The samples can be further processed using methods known to those skilled in the art to isolate molecules contained in the sample such as, for example, cells, proteins and nucleic acids (e.g., DNA and RNA).

The isolated molecules can also be further processed. For example, cells can be lysed and subjected to methods for isolating proteins and/or nucleic acids contained within the cells. Proteins and nucleic acids contained in the sample and/or in isolated cells can be processed. For example, proteins can be processed for electrophoresis, Western blot analysis, immunoprecipitation and combinations thereof. Nucleic acids can be processed, for example, for polymerase chain reaction, electrophoresis, Northern blot analysis, Southern blot analysis, RNase protection assays, microarrays, serial analysis of gene expression (SAGE) and combinations thereof.

Suitable probes can include, for example, nucleic acid probes, antibody probes, and chemical probes.

In some embodiments, the probe can be a labeled probe. Suitable labels can be, for example, a fluorescent label, an enzyme label, a radioactive label, a chemical label, and combinations thereof. Suitable radioactive labels are known to those skilled in the art and can be a radioisotope such as, for example, 32P, 33P, 35S, 3H and 125I. Suitable enzyme labels can be, for example, colorimetric labels and chemiluminescence labels. Suitable colorimetric (chromogenic) labels can be, for example, alkaline phosphatase, horse radish peroxidase, biotin and digoxigenin. Chemiluminescence labels can be, for example, alkaline phosphatase, glucose-6-phosphate dehydrogenase, horseradish peroxidase, Renilla luciferase, and xanthine oxidase. A particularly suitable label can be, for example, SYBR® Green (commercially available from Life Technologies). A particularly suitable probe can be, for example, an oligonucleotide labelled with SYBR® Green. Suitable chemical labels can be, for example, periodate and 1-Ethyl-3-[3-dimethylaminopropyl]carbodiimide hydrochloride (EDC).

It should be understood that any methods known in the art for measuring expression level of the desired protein can be used herein without departing from the scope of the present disclosure. By way of example, in one particular embodiment, the expression level is measured by: contacting a portion of the sample obtained from the patient with an antibody having specific binding affinity for protein OMA1, thereby forming a complex between the antibody and protein OMA1 in the sample; separating the complex formed in said step of contacting from antibody not bound to protein OMA1; and quantifying a signal from the complex between the antibody and protein OMA1, the signal being proportional to the expression level of protein OMA1 in the sample obtained from the subject.

In another aspect, the present disclosure is directed to a method of monitoring effectiveness of a therapy in a subject having or suspected of having a metastatic breast cancer. The method includes: measuring an expression level of protein OMA1 Zinc Metallopeptidase (OMA1) in at least a first chronological sample obtained from the subject; administering the therapy; measuring an expression level of protein OMA1 Zinc Metallopeptidase (OMA1) in at least a second chronological sample obtained from the subject, analyzing the expression level of protein OMA1 Zinc Metallopeptidase (OMA1) in at least the first chronological sample and the expression level of protein OMA1 Zinc Metallopeptidase (OMA1) in at least the second chronological sample, wherein an increase in the expression level of protein OMA1 Zinc Metallopeptidase (OMA1) in the second chronological sample as compared to the expression level of protein OMA1 Zinc Metallopeptidase (OMA1) in a first chronological sample indicates effectiveness of the therapy. It should be understood that more than two samples can be used in the methods without departing from the scope of the present disclosure.

Suitable therapies for administration in the methods describe above include chemotherapeutic agents as known in the art for treating cancer, and particularly, breast cancer. For example, in one embodiment, the therapy includes doxorubicin.

Various functions and advantages of these and other embodiments of the present disclosure will be more fully understood from the examples shown below. The examples are intended to illustrate the benefits of the present disclosure, but do not exemplify the full scope of the disclosure.

Example

In this Example, the role of the metallopeptidase OMA1 in regulation of tumor progression in breast cancer cells was analyzed.

Materials and Methods

Generation of Stable OMA1 Knockdown Cell Lines

21MT-1 cells were obtained from Dr Hamid Band at the University of Nebraska Medical Center. This cell line was isolated from metastatic pleural effusion mammary tumor specimens. The 21MT-1 cells were cultured in α-MEM media supplemented with 5% fetal bovine serum (FBS), 1% Penicillin-Streptomycin (PS), 1% L-glutamine, 20 mM HEPES, non-essential amino acids, sodium pyruvate (all stated reagents from Invitrogen), 12.5 ng/ml epidermal growth factor (EGF) and 1 µg/ml hydrocortisone (both from Sigma-Aldrich). MCF10A (ATCC CRL-10317), human normal breast tissue cell line, were cultured in DMEM/F12 (Mediatech) and supplemented with 1% L-glutamine, 1% Penicillin-Streptomycin, 5% Horse Serum, 0.1 ng/ml cholera toxin, 0.5 µg/ml hydrocortisone, 10 µg/ml insulin, and 0.02 ng/µl rhEGF (all from Sigma-Aldrich). All cells were kept in aseptic conditions, and grown in an incubator at 37° C. and 5% $CO_2$. 21MT-1 and MCF10A cells were transfected with a set of OMA1 shRNA-expressing plasmids (Origene) using Lipofectamine 3000 reagent (Thermo Fisher Scientific). The cells were allowed to recover for 24 hours in fully supplemented DMEM/F12 medium (10% FCS, 4 mM L-Glutamine, 4 mM Glucose) without antibiotics. The medium was then replaced with fully supplemented DMEM/F12 containing 3 µg/ml puromycin. Cells were selected in this medium until a week after all the cells in the control wells (mock-transfected) were dead. Medium was replaced every 3 days. Colonies of puromycin-resistant cells were then seeded in 25 $cm^2$ cell culture flasks, and tested for decrease of OMA1 expression by immunoblotting.

Cell Viability Assays

The wild type and $oma1^{-/-}$ mouse embryonic fibroblasts (24, obtained from Dr. Carlos Lopez-Otin, University of Oviedo) were seeded into 12-well plates at the density of $4\times10^4$ cells per well. DMEM medium contained 10% FCS (Thermo Fisher Scientific) and L-Glutamine (4 mM), as well as glucose (10 mM), galactose (10 mM), with or without 10 µM bis-2-(5-phenylacetamido-1,2,4-thiadiazol-2-yl)ethyl sulfide (BPTES), depending on experimental condition. Every 24 hours cells, from one well per condition were trypsinized with 0.05% Trypsin (Life Technologies), washed with Ca-, Mg-PBS, resuspended and counted in Countess Automated Cell Counter (Life Technologies). The experiment was done in 4 biological replicates, with each replicate consisting of two technical replicates. Glucose, galactose, BPTES, and L-glutamine were obtained from Sigma-Aldrich.

Imaging Techniques

Phase Images

Phase images were obtained for morphology of live cells assessment using an Axiovert 40 CFL (Zeiss) and Progres C3 (Jenoptik) camera.

Fluorescent Imaging and Actin Staining

Cells were fixed with 4% paraformaldehyde in PBS at room temperature for 20 minutes. Samples were permeabilized in 2% Triton X-100 for 15 minutes at room temperature. Actin 488 ready Probe (Life Technologies) was applied according to manufacturer instructions and incubated on fixed cells at room temperature for 30 minutes. Nuclei were visualized with DAPI stain by 5-minutes, or with Hoechst 33342 stain by 10 minutes, incubation at room temperature in a 1 µg/ml solution. Images were obtained using Axiovert 40 CFL (Zeiss) and a Progres C3 (Jenoptik) camera with an X-Cite series 120Q (Lumen Dynamics) lamp utilizing FITC or DAPI filter (Chroma).

BrdU Staining

Proliferation was assessed utilizing 5-Bromo-2-Deoxyuridine (BrdU) which incorporates into newly formed DNA during proliferation and is then detectable by Alexa Fluor 488 conjugated antibody (Life Technologies). This was performed by first incubating the breast cancer cell monolayer in 10 µM BrdU in culture media solution for 24 hours at 37° C. prior to fixing the cells in a suspension of 4% paraformaldehyde. The cells were permeabilized with 0.1% Triton X-100 in PBS, DNA denatured with 0.03% DNase in PBS, and blocked with 1% BSA in PBS. Finally, the BrdU was detected by incubating the cells in anti-BrdU antibody (Life Technologies) in 1% BSA in PBS overnight at 4° C., washed two times in 1×PBS and florescence intensity quantified by FACSCanto 11 (Becton-Dickinson) in the green channel (ex. 495, em. 520; 100,000 total events per read) against cells that had not been treated with BrdU.

Membrane Potential Measurement

Cells were seeded overnight in 6-well plates at 500,000 cells per well. Prior to the experiment, cells were either treated with vehicle (DMSO) or CCCP (final concentration 2 uM) for 1 hour. Following the treatments, cells were trypsinized with 0.05% trypsin, washed 3× with PBS and resuspended in 1 ml PBS for staining. Cells were stained on ice in 50 nM TMRM (Sigma) for 15 minutes, and subsequently assayed on Cytek DxP10 flow cytometer (Cytek Biosciences). TMRM fluorescence was measured using 561 nm excitation, and 580/20 nm emission; 50,000 cells were assayed in each experiment. Results were analyzed and plotted using FlowJo 10 software (FlowJo).

Mitochondrial Imaging

Mitochondrial morphology was visualized utilizing MitoTrackerR Red CMXRos (Life Technologies) according to manufacturer's instructions. In short, after 24 hours the culture media was removed and replaced with serum-free, translucent phenol red-free DMEM containing 300 nM MitoTrackerR probe and incubated at 37° C. for 30 minutes. Cells were then washed three times with warm 1×PBS and serum free, translucent phenol-red free DMEM was added for viewing with an Olympus FV500 Inverted Confocal Microscope.

Quantitative Real-Time PCR qRT-PCR was performed using standard qRT-PCR program on ABI 7900HT qRT-PCR cycler (Applied Biosystems), using validated qRT-PCR primers (Realtimeprimers.com). Expression data for AFG3L2, CLPP, SPG7 and HSPD1 were normalized using qRT-PCR for Actin B. CYBR-Green qPCR mix was obtained from Life Technologies. The experiment was done in 3 biological replicates, each consisting of 4 technical replicates.

Western Blotting

Whole cell lysate from cell cultures was prepared using RIPA buffer (1×PBS containing 1% IGEPAL CA-630, 0.5% sodium deoxycholate, 0.1% sodium dodecyl sulfate (SDS), 1 mM phenylmethylsulfonyl fluoride (PMSF) and protease inhibitor cocktail). Cells were washed three times with ice cold 1×PBS, lysed in RIPA buffer on ice for 10 minutes, centrifuged at 10,000×g for 10 minutes at 4° C. and clear cell lysate was collected. Samples were centrifuge at 10,000×g for 20 minutes at 4° C., supernatant was transferred to 0.2 µM microcentrifuge filters (ThermoFisher Scientific), and centrifuge at 10,000×g for 10 minutes at 4° C. to collect clear cell lysate. Protein concentrations were determined using Coomassie Plus Assay reagent (Pierce). 10 µg of total protein was separated by 7.5% SDS-polyacrylamide gel electrophoresis and transferred to Immobilon P membranes (Millipore) using transfer buffer (25 mM Tris, 192 mM glycine, 10% methanol). Membranes were blocked with 5% skimmed milk for 2 hours at room temperature (RT); thereafter, membranes were incubated with either anti-EMT markers IgG panel (GeneTex GTX300096, 1:1000), anti-OMA1 IgG (Aviva Systems Biology ARP52818_P050, 1:1000), anti-AFG3L2 IgG (Aviva Systems Biology ARP46780_P050, 1:1000), anti-HSPD1 (Aviva Systems Biology AVARP09014_P050, 1:1000) anti-HIF1α IgG (Aviva Systems Biology ARP38054_P050, 1:1000) or anti-GAPDH IgG (Millipore ABS16, 1:4000) for overnight at 4° C. Membranes were next incubated with HRP-linked goat anti-rabbit IgG (Santa Cruz Biotechnology sc2054, 1:4000) for 1 hour at room temperature. All membranes were visualized using ECL and exposure to ECL Hyperfilm (Pierce). Densitometry analysis of bands was performed using Image Studio™ Lite Software v.4.0 (LI-COR Biosciences).

In Vitro Migration Assay

21MT-1 or MCF10A cells (control and shOMA1) were plated into new 12-well plates as confluent monolayers. Three vertical scratches were made per well (use of a 10 µl pipette tip), and cell debris was washed away with 1×PBS prior to taking the time=0 hour photos. Additional photos were taken at 24 and 48 hour-time points. The cells were supplemented in complete 21MT-1 media for the entire migration assay. ImageJ software was used to quantify the scratch width (arbitrary units) changes at each time point. A total of 27 scratch width data points were taken for each sample type at each time point (3 scratches per well×3 pictures per scratch×3 biological duplicates per sample type).

Bioenergetic Profiling

Cells were seeded at the density of $5\times10^4$ cells per well 24 hours before the experiment in Seahorse medium (Agilent Technologies/Seahorse Bioscience), supplemented with L-Glutamine (4 mM), as well as Glucose (10 mM), Galactose (10 mM), BPTES (10 µM) and Pyruvate (2 mM), depending on experimental condition. After 24 hours, cells were washed twice with 1 ml Seahorse medium per well. Then, cells were supplemented with 0.5 ml fresh Seahorse medium supplemented with L-Glutamine (4 mM), as well as Glucose (10 mM), Galactose (10 mM), BPTES (10 µM) and Pyruvate (2 mM), depending on experimental condition, and kept for 1 hour in non-$CO_2$ incubator at 37° C. Then, OCR was measured under basal conditions and addition of oligomycin (1 µM), FCCP (1 µM), and rotenone/antimycin A (0.5 µM). Measurements were performed using standard Mito Stress protocol on XFe24 Extracellular Flow Analyzer (Agilent Technologies/Seahorse Bioscience). Oligomycin, FCCP, and rotenone/antimycin A were obtained as a part of Mito Stress Kit (Agilent Technologies/Seahorse Bioscience). Glucose, Galactose, BPTES, L-Glutamine, and Pyruvate were obtained from Sigma-Aldrich. The experiment was done in 4 biological replicates, with each replicate consisting of 3-4 technical repeats per condition.

Bioinformatics and Statistical Analyses

Overall survival in patients was analyzed using the results from TCGA studies of breast adenocarcinoma (https://cancergenome.nih.gov). The data regarding two groups of patients—with low (n=45) and high (n=180) levels of OMA1 expression—were analyzed using the cBioPortal online platform (http://www.cbioportal.org). Log-rank statistical test was used to compare the survival distribution of these two samples.

Statistical analyses were performed using Microsoft Excel 2013 Analysis ToolPak and GraphPad Prism 4 software. In each case, the results of at least three independent experiments were analyzed using one-way ANOVA or Student's t-test. The p values <0.05 were considered statistically significant.

Results

OMA1-Deficient Cells Exhibit Signs of Metabolic Reprogramming

A recent study revealed that upon culturing in low glucose medium, OMA1-deficient mouse embryonic fibroblasts (MEFs) are compromised in their ability to maximize their bioenergetic output and appear to rely on compensatory aerobic glycolysis, as indicated by an increased extracellular acidification rate (Bohovych et al., Sci Rep. 2015; 5: 13989 and FIG. 1A). This observation likely reflects partial metabolic reprogramming and suggests that oma1$^{-/-}$ MEFs are probably more reliant on anaplerotic metabolism. As such, these cells are expected to replenish their citrate levels through enhanced utilization of glutamine that is metabolized via reductive carboxylation—enzymatic conversion of glutamine to glutamate, which is then modified to α-ketoglutarate, followed by its conversion to oxaloacetate and then citrate. Thus, OMA1-deficient cells are expected to be more sensitive to inhibition of glutaminase (GLS)—a key enzyme mediating the first step in the above chain of reactions.

Figure 1B:
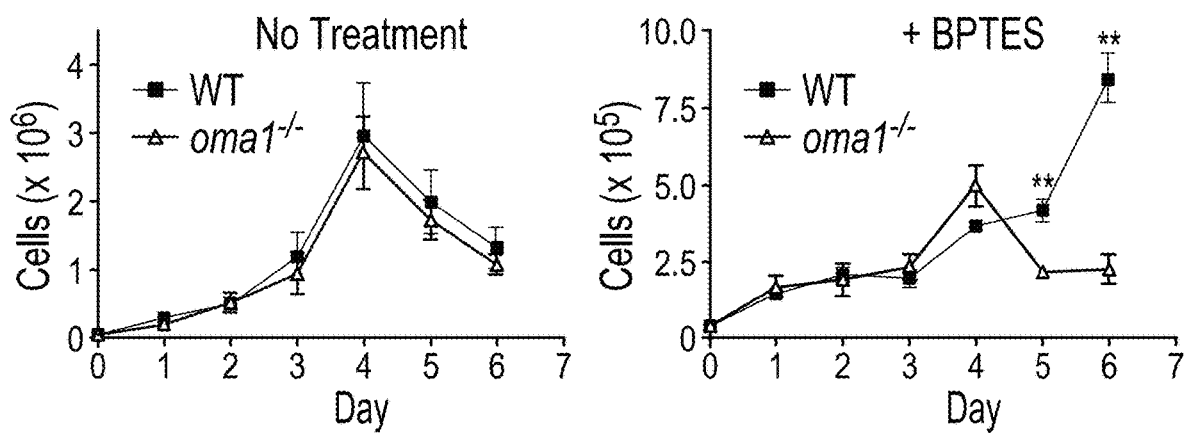
Figure 1C:
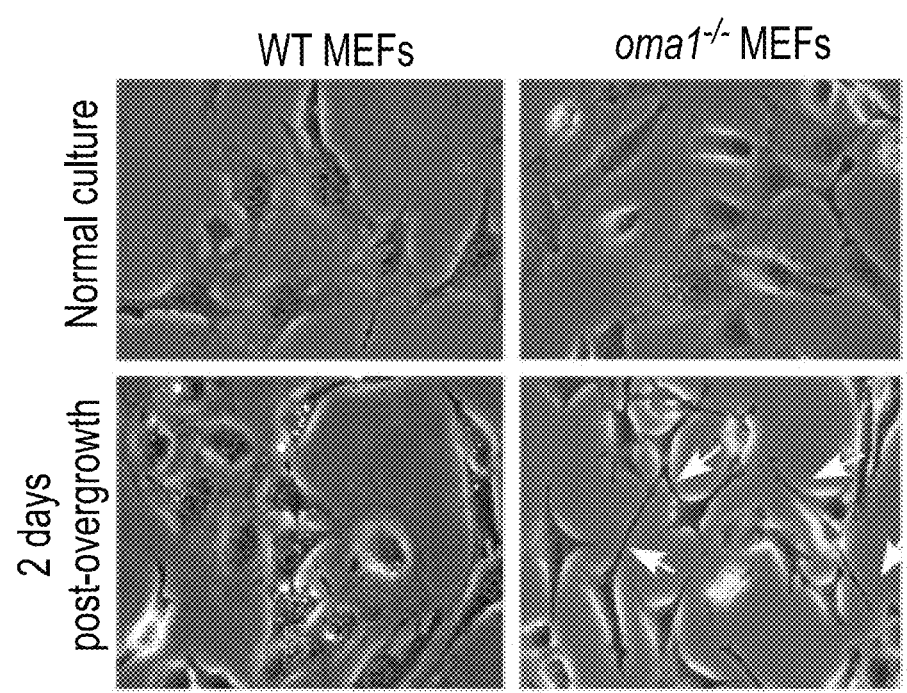
Figure 1D:
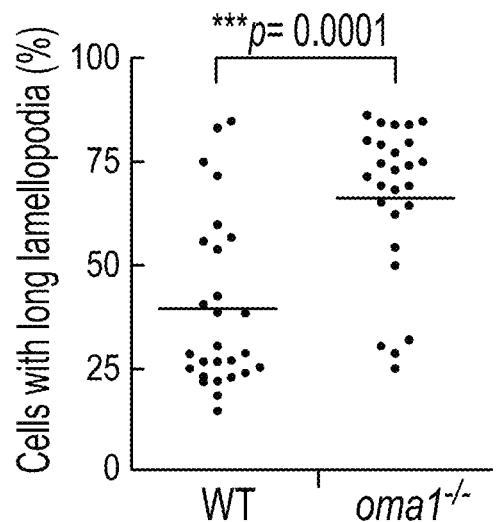
Figure 1E:
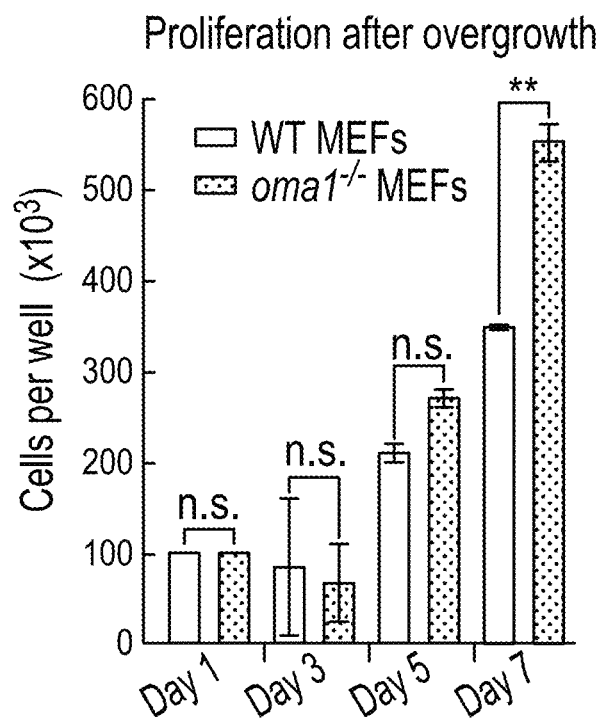
Figure 1F:
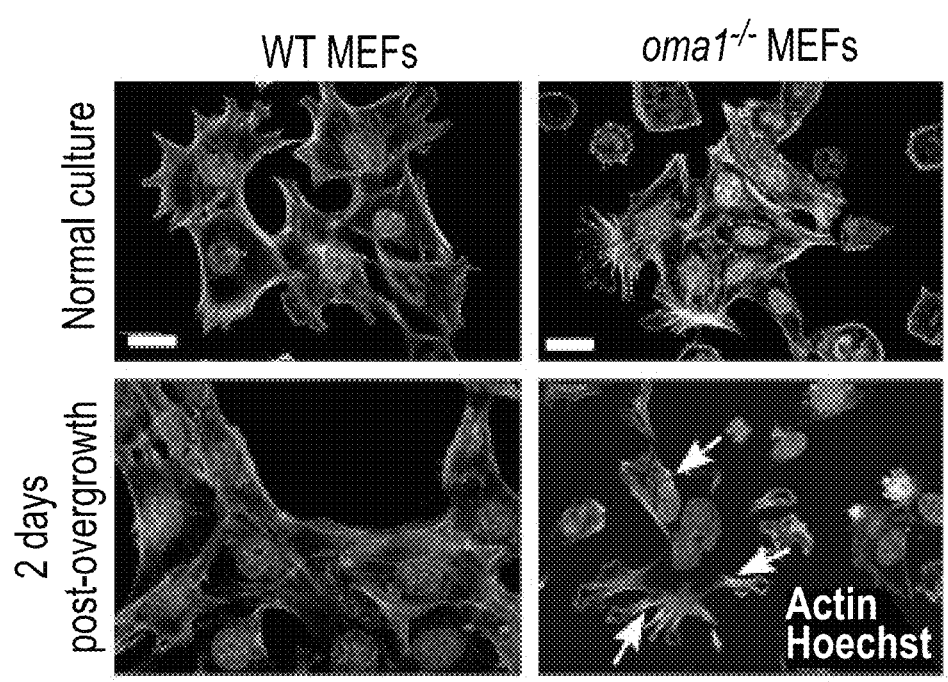

To test this postulate, proliferation of wild type and oma1$^{-/-}$ cells cultured in either low glucose or galactose-containing medium in the presence or absence of 10 μM bis-2-(5-phenylacetamido-1,2,4-thiadiazol-2-yl)ethyl sulfide (BPTES)—a specific small molecule inhibitor of GLS was analyzed. While proliferation of the cells in question was nearly identical under normal conditions, oma1$^{-/-}$ MEFs proliferated at much slower rates than wild type cells in the presence of BPTES (FIG. 1B). These observations prompted us to examine the ability of the WT and oma1$^{-/-}$ MEFs to re-enter the proliferative cycle after aging-induced quiescence, a process known to require normal mitochondrial function. Contact-inhibited quiescent WT and oma1$^{-/-}$ MEFs were cultured for 7 days with fresh medium added every 2 days. Following such incubation, the proliferative properties of these post-quiescent cells were tested. While growth characteristics and morphology of the young WT and oma1$^{-/-}$ cells were virtually indistinguishable (FIG. 1C), the post-quiescent oma1$^{-/-}$ MEFs formed lamellopodia-like structures (FIGS. 1C & 1D) and proliferated significantly faster than control MEFs (FIG. 1E). Likewise, the post-quiescent growth of oma1$^{-/-}$ MEFs was characterized by higher cell spreading when compared to the wild type control. Moreover, consistent with the observed lamellopodia structures, post-quiescent oma1$^{-/-}$ MEFs displayed abnormal actin distribution patterns (FIG. 1F) resembling rearrangements reported in neoplasms. These results further highlight metabolic and morphological alterations in OMA1-deficient mammalian cells, suggesting consequent changes in their proliferative properties.

Figure 2A:
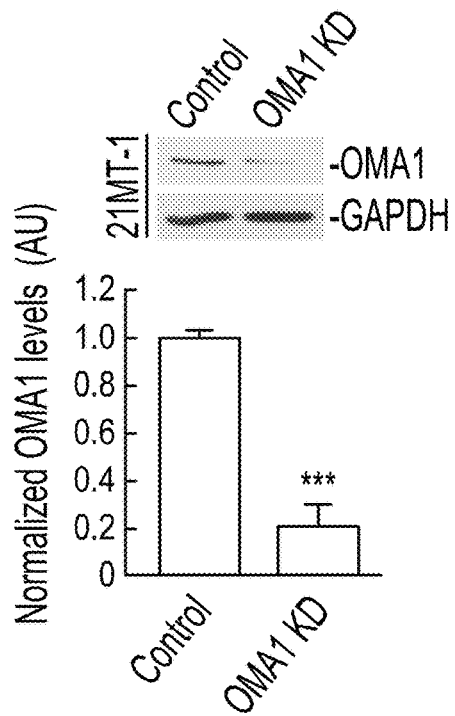
FIGS. 2A-2H show that OMA1 depletion in metastatic breast cancer cells promoted lamellopodia formation.
Figure 2B:
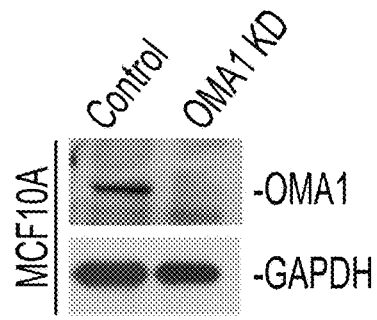
Figure 2C:
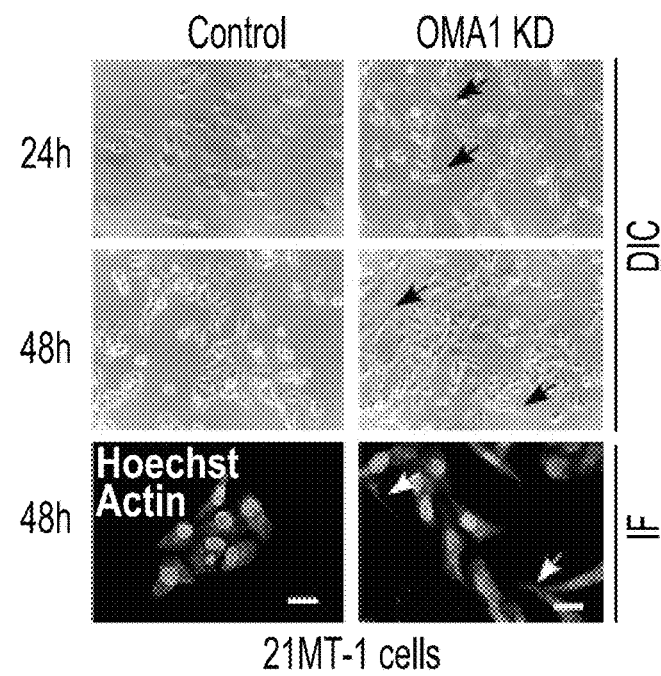
Figure 2D:
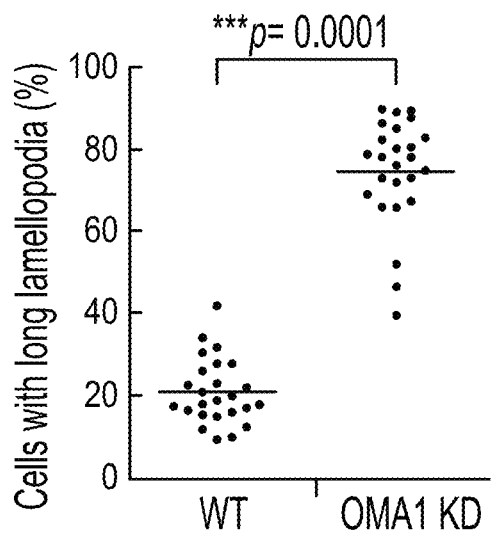
Figure 2E:
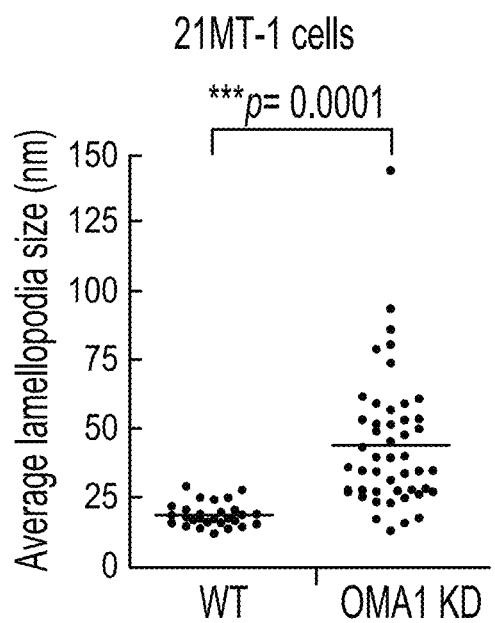
Figure 2F:
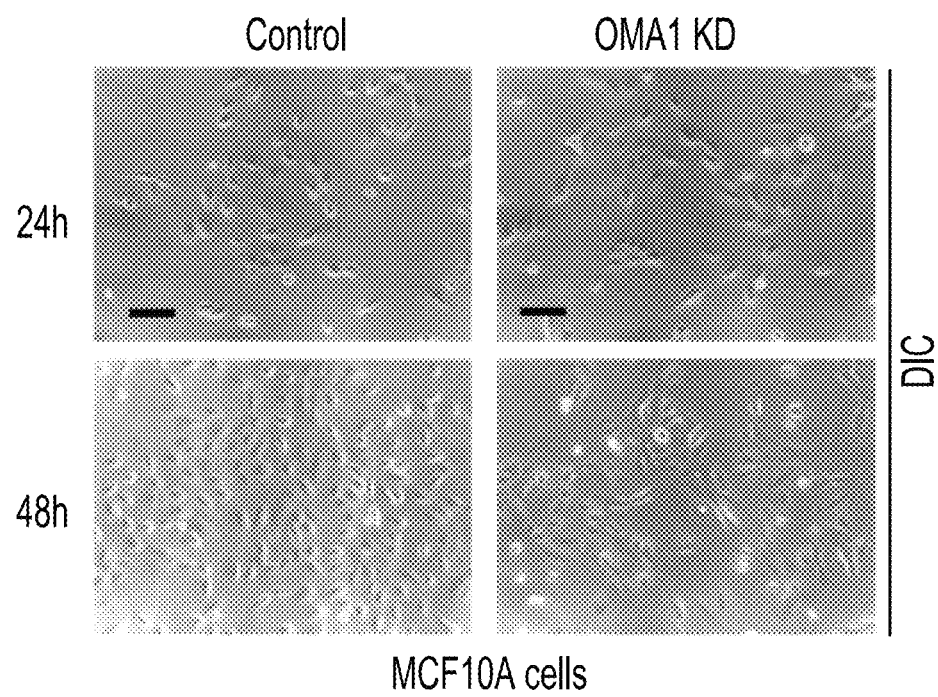
Figure 2G:
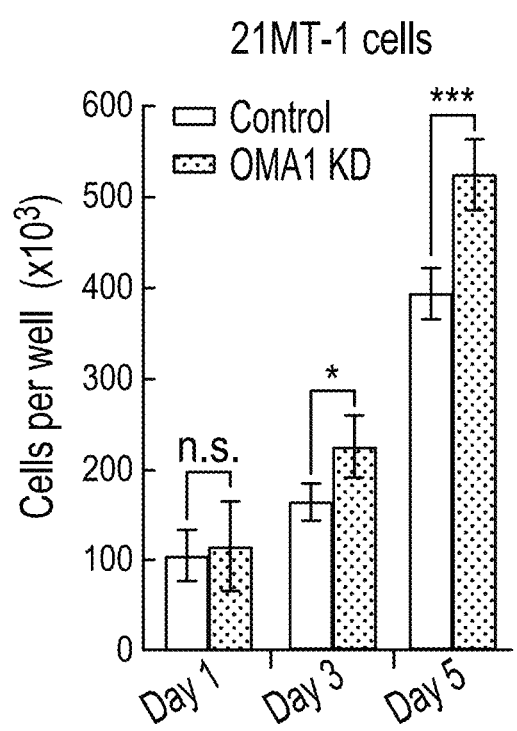
Figure 2H:
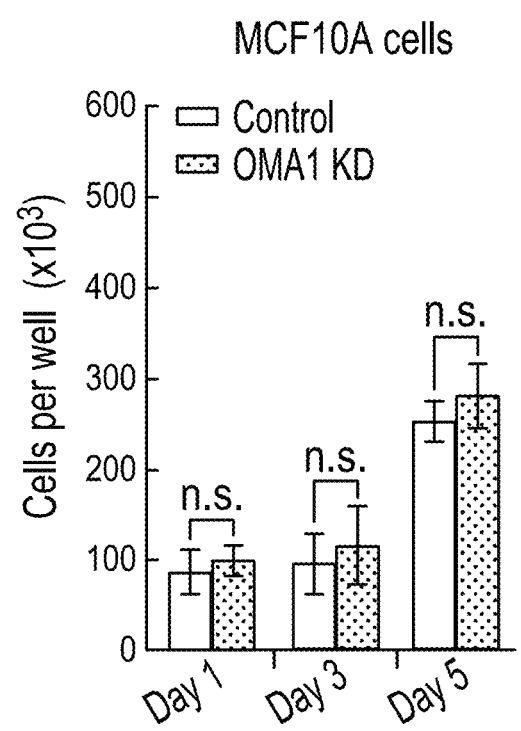

Loss of OMA1 Causes Lamellopodia Formation and Mitochondrial Fragmentation in Human Breast Adenocarcinoma Cell Lines Formation of focal adhesions is a hallmark of tumorigenesis. The results of the above analyses in MEFs suggest that loss of OMA1 may be related to neoplastic transformation. Moreover, OMA1 protein levels were reported to be extremely low in breast and testicular cancer tissues, and in lymphomas. It was thus hypothesized that OMA1 function may be attenuated in these cancers and such an impediment may be an important contributor to malignancy. To test this hypothesis, stable knockdowns of OMA1 were generated in non-tumorigenic breast epithelial cells (MCF10A) and patient-derived breast cancer cells isolated from metastatic pleural effusion mammary tumor specimen (21MT-1) cells using OMA1-specific shRNAs Immunoblotting with an anti-OMA1 antibody confirmed efficient depletion of the protease in cells expressing OMA1 shRNA, but not the scrambled control (FIGS. 2A & 2B). Transfection of 21MT-1 cells with OMA1-targeting shRNAs caused over 80% reduction in endogenous OMA1 protein as compared to control and cells transfected with scrambled shRNAs. Microscopy of OMA1-depleted 21MT-1 cells revealed enhanced lamellopodia formation even at 24 hours of culture; this effect was even more pronounced after 48 hours of culturing (FIGS. 2C-2E). Remarkably, this was not the case for OMA1-depleted MCF10A cells (FIG. 2F). Also OMA1-depleted 21MT-1 cells demonstrated higher proliferation rates compared to control 21MT-1 cells, while no significant change in proliferation rates were observed in OMA1-depleted and control MCF10A cells (FIGS. 2G & 2H). Strikingly, these findings parallel the observations in oma1$^{-/-}$ MEFs.

Figure 3A:
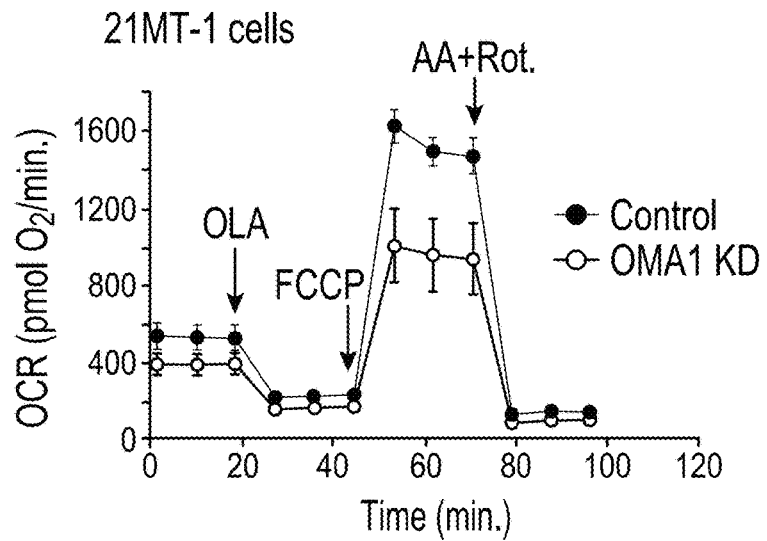
FIGS. 3A-3C show that OMA1 depletion in 21MT-1 cells altered their bioenergetic and metabolic properties.
Figure 3B:
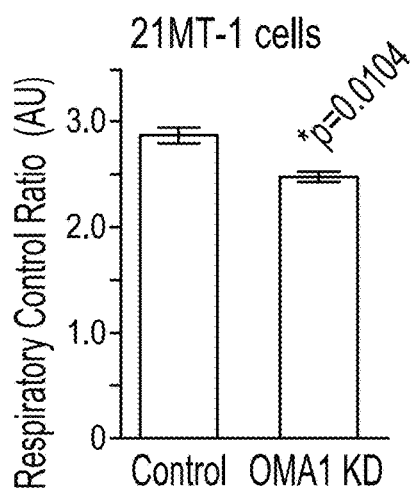
Figure 3C:
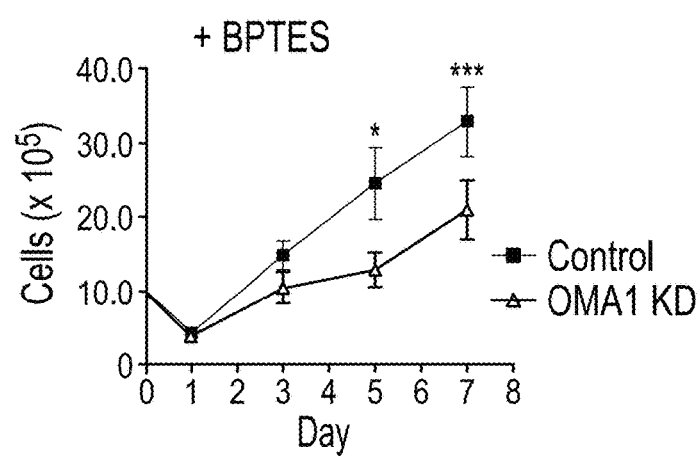
Figure 3D:
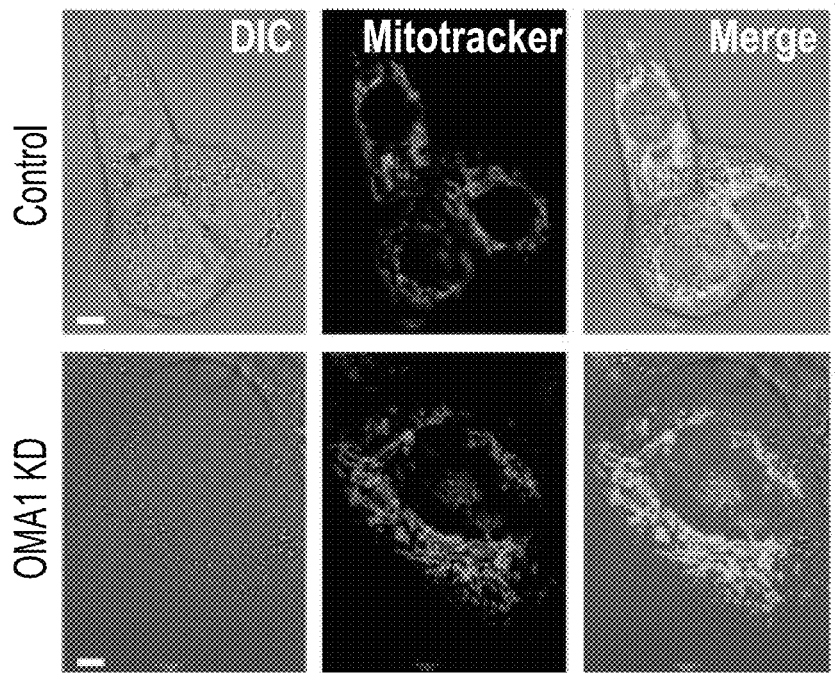
FIGS. 3D & 3E show that loss of OMA1 did not significantly alter mitochondrial network organization, but caused actin branching in 21MT1 cells.
Figure 3E:
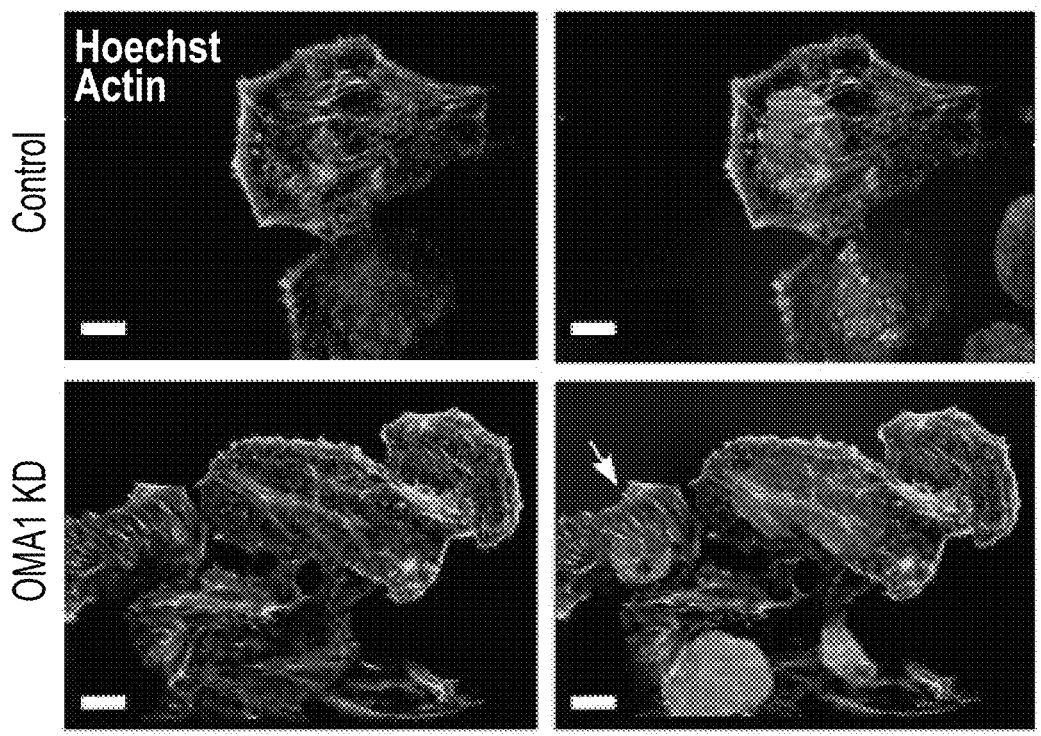

Bioenergetics profiling of OMA1-deficient 21MT-1 cells revealed that similarly to oma1$^{-/-}$ MEFs, these cells were unable to maximize their respiration in response to mild uncoupling (FIG. 3A) and had significantly lower respiratory control ratios (FIG. 3B) when cultured in the respiration-enforcing medium containing 10 mM galactose. Moreover, just like oma1$^{-/-}$ MEFs, OMA1-depleted 21MT-1 cells exhibited marked increase in sensitivity to the glutaminase inhibitor BPTES (FIG. 3C); all indicative of a bioenergetic deficit. To probe and visualize the effect of OMA1 knockdown (KD) on mitochondrial morphology and integrity of 21MT-1 cells, the mitochondria was imaged using the fluorescent stain MitoTrackerR Red (FIG. 3D). The control 21MT-1 cells depicted the typical fiber-like morphology indicating healthy mitochondria. When OMA1 was depleted from the 21MT-1 cells, a slightly more dense or bulky mitochondrial network with perinuclear clustering was observed (FIG. 3D). In addition to differences in the spatial distribution and clustering of the mitochondrial reticulum seen in the OMA1 KD 21MT-1 cells, mitochondria within the clusters appeared as slightly thicker and shorter segments as compared to control. Such changes likely reflect alterations in the mitochondrial dynamics and/or cristae remodeling associated with inactivation of OMA1-mediated processing of the IM GTPase, OPAL Of note, and in line with the above observations in oma1$^{-/-}$ MEFs, the steady-state levels of the key components of mitochondrial fusion (mitofusins MFN1 and MFN2, and long and short isoforms of OPA1) and fission (DRP1) machinery remained unaltered in OMA1-depleted 21MT-1 cells. The impact of OMA1 KD on 21MT-1 cell morphology was further investigated by immunostaining of the actin cytoskeletal structure (FIG. 3E). Remodeling of actin cytoskeleton influences cell migration and invasion. Genetic depletion of OMA1 led to a substantial change in the 21MT-1 cell appearance, resulting in larger cell bodies and a stretched morphology. Additionally, the OMA1 KD 21MT-1 cells exhibited considerably more stress actin fibers traversing the cytoplasm than control 21MT-1 cells. Interestingly, these effects were not observed in OMA1-deficient non-tumorigenic MCF10A mammary epithelial cells (FIG. 2F). These data suggest that loss of OMA1 promotes lamellopodia formation and significant remodeling of the cell and mitochondrial morphology in breast cancer cells.

Figure 4A:
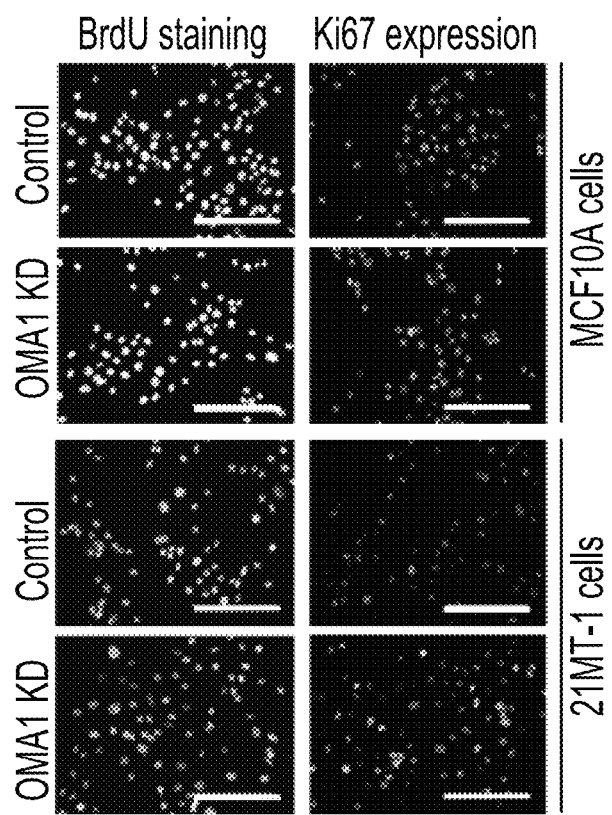
FIGS. 4A-4F show that OMA1 limited proliferation and migration of 21MT-1 metastatic breast adenocarcinoma cells.
Figure 4B:
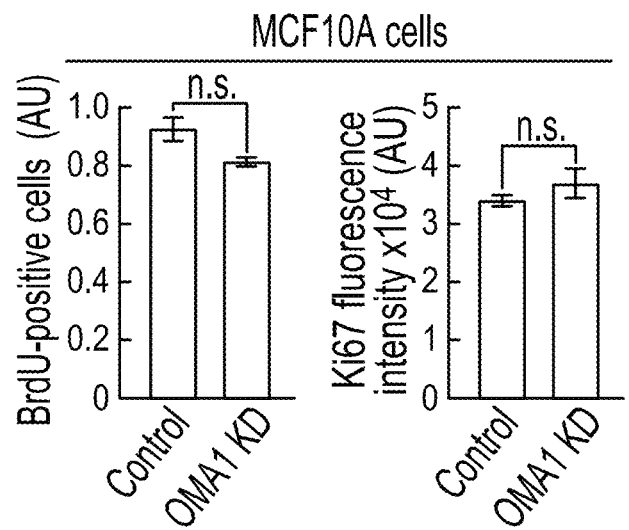
Figure 4C:
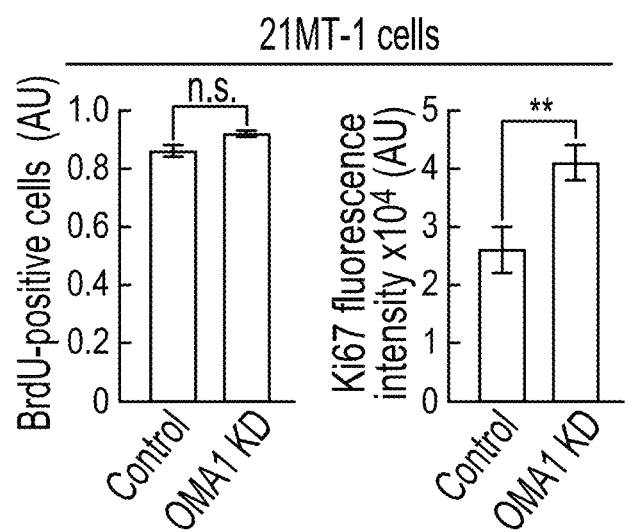

Suppression of OMA1 Increases Proliferation and Migration of Metastatic Breast Adenocarcinoma Cells Proliferation and lamellopodia-like structures play a key role in cancer cell invasion. Increased appearance of these structures in OMA1-depleted 21MT-1 cells may indicate enhanced invasiveness of these cells and deregulation of the cell cycle. This hypothesis was examined by immunostaining control and OMA1-deficient 21MT-1, and MCF10A cells with BrdU and Ki67 antibodies (FIG. 4A). BrdU is commonly used to determine the rate of cell proliferation and is a specific marker for the S-phase where Ki67, a nuclear protein, is a commonly used clinical marker to determine the proliferative state of tumor cells in all phases of the cell cycle. There were no significant changes observed by BrdU staining for OMA1-deficient and wild type MCF10A cells (FIG. 4B). Remarkably, the Ki67 expression was higher in the OMA1-depleted 21MT-1 cells, indicating that the tumor cells are in a more proliferative state relative to normal 21MT-1 cells (FIG. 4C). Interestingly, OMA1-deficient MCFA10A normal breast epithelial cells did not have any significant effect in the Ki67 expression as compared to control cells, indicating that the phenomena is specific to neoplasms.

Figure 4D:
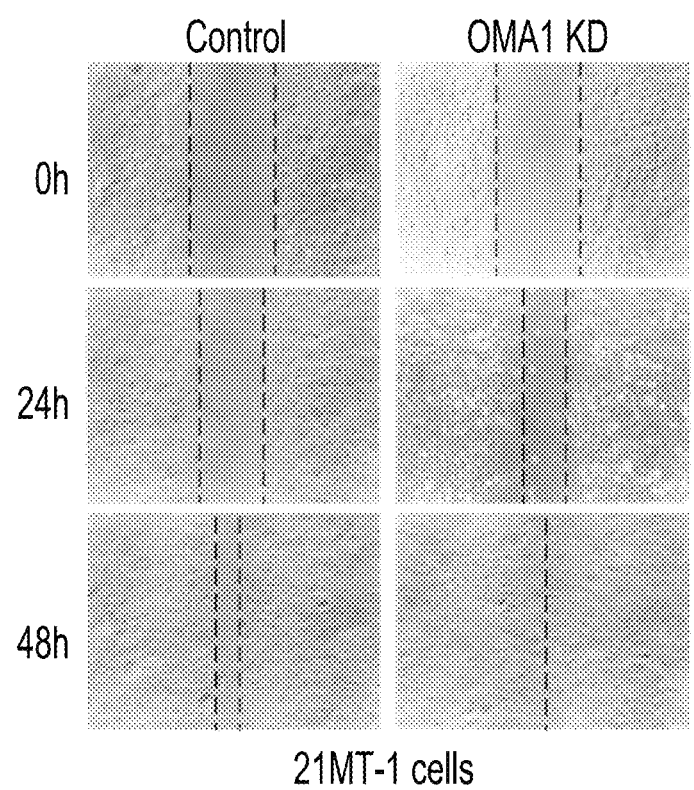
Figure 4E:
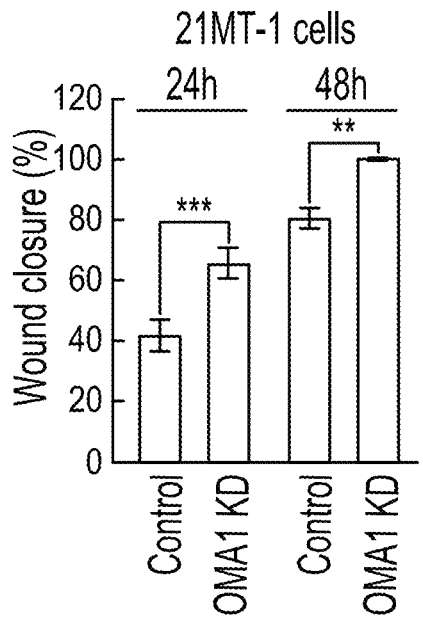
Figure 4F:
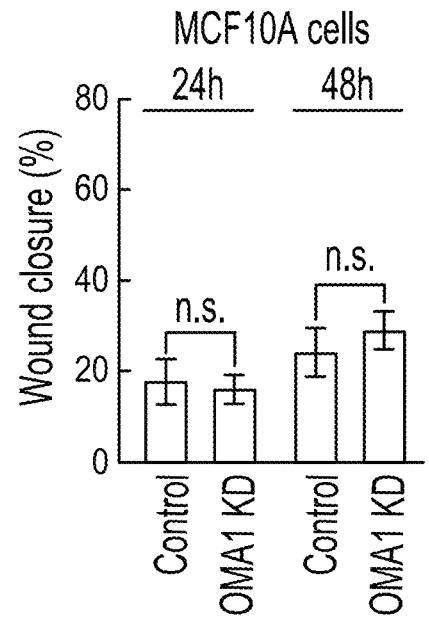

To further interrogate the exciting link between OMA1 silencing and the observed enhancement of cellular migration, migratory potential of the metastatic breast cancer cells was examined with normal and reduced levels of the protease. To this end, a scratch was made in a sub-confluent cell monolayer in control, and OMA1 knockdown 21MT-1 cells and cells were allowed to migrate into the cell-free area. Loss in OMA1 resulted in significantly higher migration in 21MT-1 cells at both 24 and 48 hours compared to control group (FIGS. 4D & 4E). In contrast, OMA1 depletion had no effect on migratory properties of non-cancerous MCF10A cells (FIG. 4F). These data suggest that loss of OMA1 function in pre-metastatic breast adenocarcinoma cells promotes migration of breast cancer cells and potentially enhances the metastatic behavior of the tumor.

OMA1 Deficiency Augments Invasiveness of Breast Cancer Cells by Inducing Epithelial to Mesenchymal Transition (EMT)

Figure 5A:
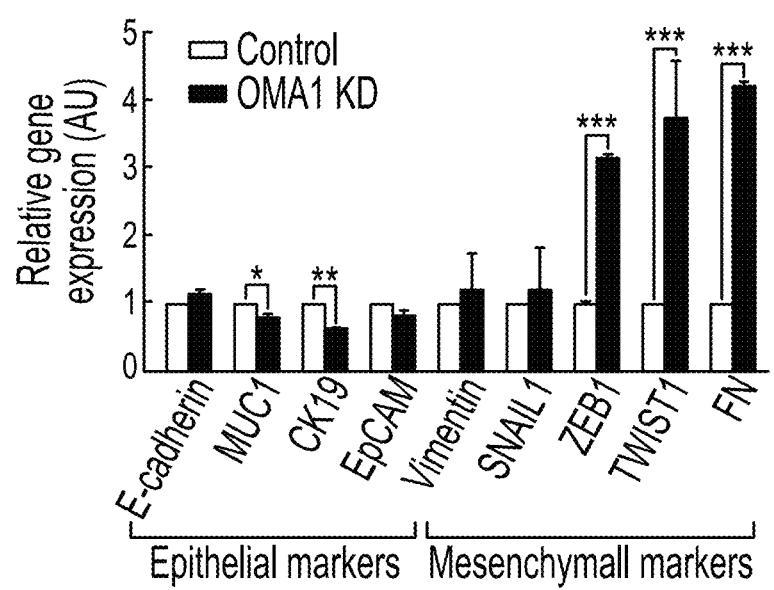
FIGS. 5A & 5B show that OMA1 deficiency enhanced invasiveness of breast cancer cells by inducing epithelial to mesenchymal transition (EMT).
Figure 5B:
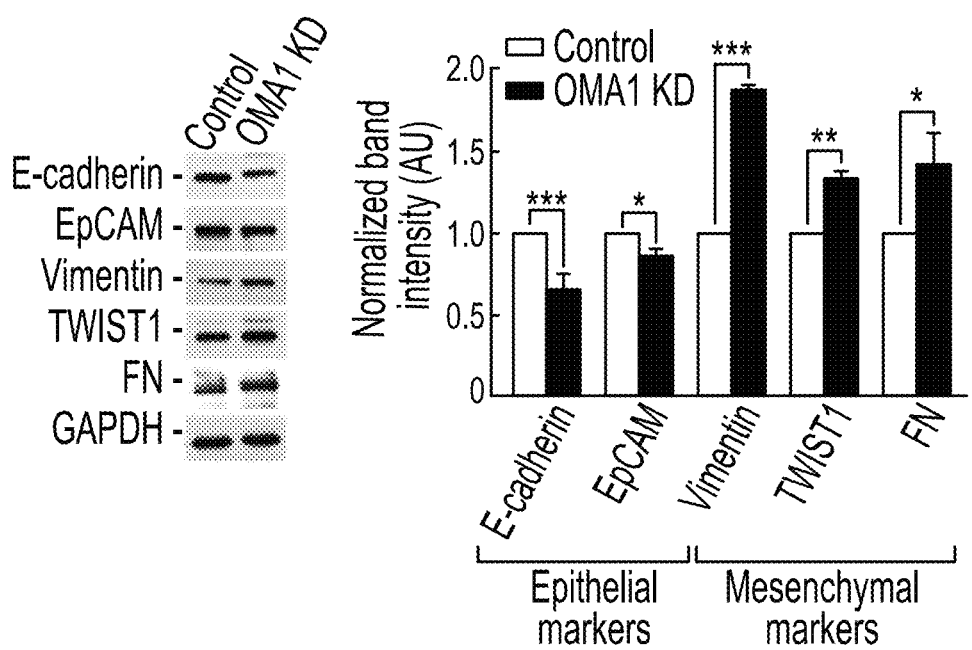

It was further investigated whether OMA1 depletion may be inducing epithelial to mesenchymal transition (EMT) in tumor cells. EMT is a transient process during which epithelial cancer cells acquire molecular alterations that facilitate the loss of epithelial features and gain a mesenchymal phenotype. This process is implicated during developmental stages and carcinogenesis, and is characterized by phenotypic and molecular changes leading to increased invasive and metastatic capabilities of cancer cells and drug resistance. When compared to control, 21MT-1 shOMA1 cells had a significantly lower gene expression of epithelial markers, cytokeratin 19 (CK19) (1.5-fold decrease) and MUC1 (2-fold decrease), indicating a loss in epithelial features of the cell (FIG. 5A). Reciprocally, OMA1-deficient 21MT-1 cells displayed substantially higher expression levels of key mesenchymal markers: ZEB1 (3-fold increase), TWIST1 (3.5-fold enhancement), and fibronectin (FN) (4-fold increase) (FIG. 5A). These EMT markers were further examined at the protein level by immunoblotting (FIG. 5B). A similar trend was observed with a significant decrease in epithelial markers (E-cadherin, EpCAM) and an increase in mesenchymal markers (Vimentin, FN, and TWIST1) in the OMA1 deficient 21MT-1 cells (FIG. 5B).

Thus, loss of OMA1 induces EMT in breast cancer cells suggesting a plausible role of OMA1 in suppressing aggressiveness and metastatic potential of breast cancer cells.

Loss of OMA1 Induces Expression of Canonical UPRmt Genes in Breast Cancer Cells

To gain insight into the potential mechanisms underpinning enhanced proliferative capacities of metastatic OMA1 knock down breast 21MT-1 cells, several potential scenarios were analyzed. The involvement of reactive oxygen species (ROS) and hypoxic signaling were ruled out as OMA1-deficient 21MT-1 cells exhibited neither elevated ROS production, nor appreciable stabilization of HIF1a, relative to control cells. Similarly, no significant changes in the nuclear to mitochondrial DNA ratio were observed in these cells—likely reflective of no alterations in mitochondrial proliferation and content.

Figure 6A:
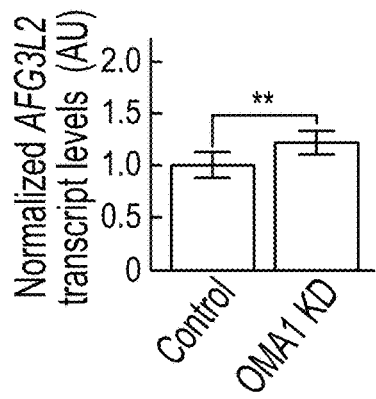
FIGS. 6A-6F show that loss of OMA1 in 21MT-1 cells drove mitochondrial unfolded protein response.
Figure 6B:
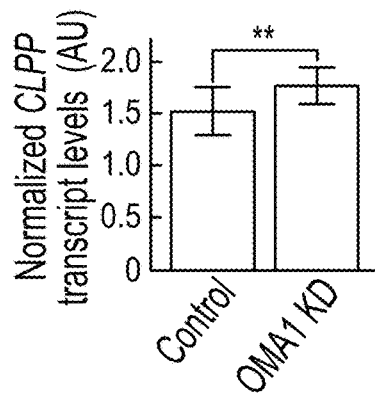
Figure 6C:
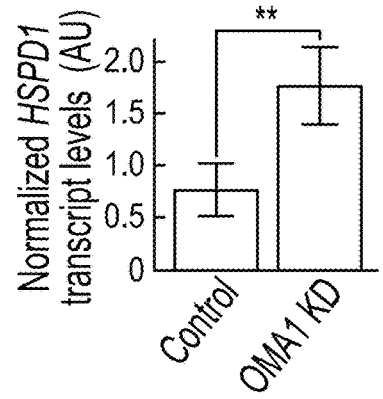
Figure 6D:
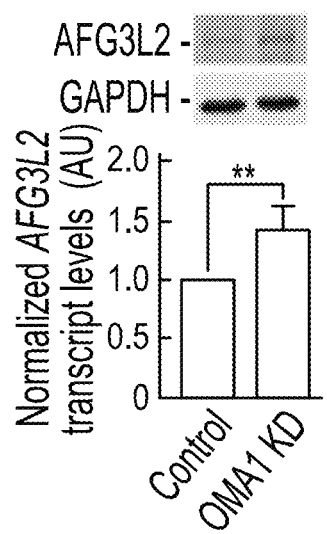
Figure 6E:
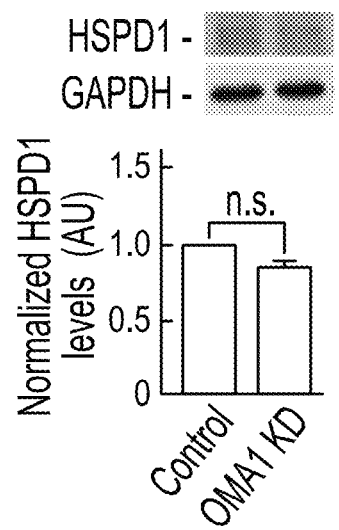
Figure 6F:
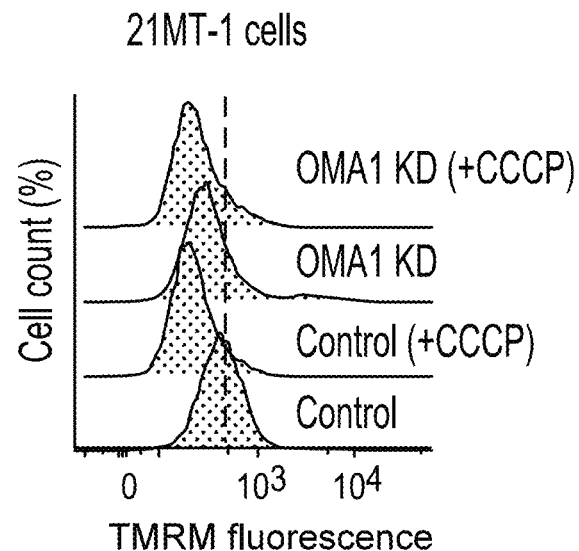
Figure 7:
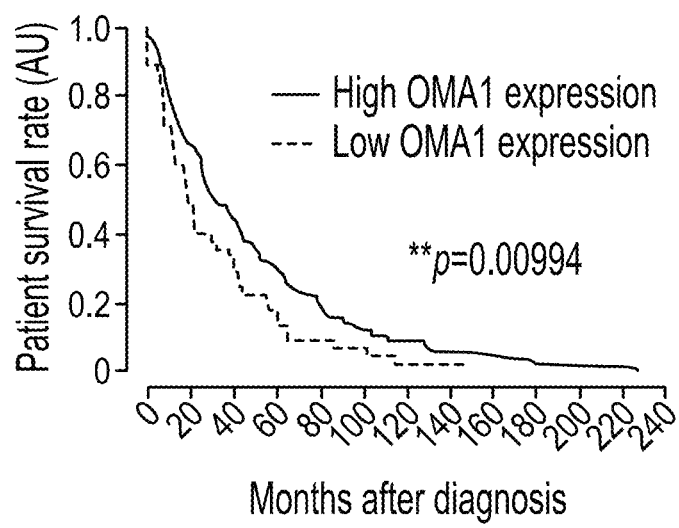
FIG. 7 shows that OMA1 expression levels correlated with patient survival in breast cancer. Kaplan-Meier estimation analysis of an overall survival for TCGA breast adenocarcinoma patients with high (n=180 cases) or low (n=45 cases) OMA1 expression levels. Log rank test identified a significant association between high OMA1 levels and better survival in this type of cancer (p-value 0.00994).

Metabolic adaptation to promote survival or proliferation of cells with mitochondrial dysfunction appears to be related to the mitochondrial unfolded protein response (UPRmt). It was therefore tested if loss of OMA1 might result in UPRmt activation. Quantitative real-time PCR and immunoblot analyses revealed that 21MT-1 cells depleted for OMA1 exhibited increased expression of several canonical UPRmt genes on both the transcript (FIGS. 6A-6C) and protein levels (FIG. 6D). For some of the UPRmt genes like HSPD1 (FIG. 6E), an increase was detected in transcript but not in the steady-state protein levels. This is likely due to additional post-transcriptional events associated with mitochondrial stress and UPRmt. The enhanced UPRmt is consistent with substantial decrease in the basal mitochondrial membrane potential in OMA1 KD 21MT-1 cells (FIG. 6F), which is likely associated with attenuation of mitochondrial protein import and enhanced stabilization of UPRmt-mediating transcription factors such as ATF5. Of note, a similar defect is readily observed in oma1$^{-/-}$ MEFs (FIG. 2F). These data suggest that loss of OMA1 leads to UPRmt activation and that sustained up-regulation of this signaling pathway is a likely contributor to the enhanced invasiveness of metastatic breast cancer cells.

As shown herein, depletion of OMA1 enhances formation of lamellopodia, increased Ki67 expression, and induction of EMT markers. Concurrently, loss of OMA1 is associated with alterations in mitochondrial protein homeostasis, as reflected by enhanced expression of canonic mitochondrial unfolded protein response genes. These changes significantly increase migratory properties in metastatic breast cancer cells, indicating that OMA1 plays a critical mechanistic role in suppressing metastatic competence of breast tumors.

What is claimed is:
1. A method of detecting a decrease in an expression level of protein OMA1 Zinc Metallopeptidase (OMA1) in a subject at risk or having metastatic breast cancer, the method comprising:
measuring an expression level of protein OMA1 in a sample obtained from the subject by contacting a portion of the sample with an antibody having specific binding affinity for protein OMA1, thereby forming a complex between the antibody and protein OMA1 in the sample, separating the complex formed in said step of contacting from antibody not bound to protein OMA1, and quantifying a signal from the complex between the antibody and protein OMA1, the signal being proportional to the expression level of protein OMA1 in the sample; and comparing the expression level of protein OMA1 in the sample with a protein OMA1 reference expression level using an imaging device.

2. The method according to claim 1, wherein said sample is selected from the group consisting of serum, plasma, and whole blood.

3. The method according to claim 1, wherein said step of measuring comprises an immunoassay procedure.

4. The method according to claim 3, wherein the immunoassay procedure comprises an enzyme-linked immunoassay (ELISA).

5. The method according to claim 3, wherein the immunoassay procedure comprises a sandwich assay format.

6. A method of monitoring effectiveness of a therapy in a subject having or suspected of having a metastatic breast cancer, the method comprising: measuring an expression level of protein OMA1 Zinc Metallopeptidase (OMA1) in at least a first chronological sample obtained from the subject; administering the therapy; measuring an expression level of protein OMA1 Zinc Metallopeptidase (OMA1) in at least a second chronological sample obtained from the subject, analyzing the expression level of protein OMA1 Zinc Metallopeptidase (OMA1) in at least the first chronological sample and the expression level of protein OMA1 Zinc Metallopeptidase (OMA1) in at least the second chronological sample, wherein an increase in the expression level of protein OMA1 Zinc Metallopeptidase (OMA1) in the second chronological sample as compared to the expression level of protein OMA1 Zinc Metallopeptidase (OMA1) in a first chronological sample indicates effectiveness of the therapy.

7. The method according to claim 6, wherein the therapy is a chemotherapeutic.

8. A method of diagnosing and treating metastatic breast cancer in a subject in need thereof, the method comprising:
measuring an expression level of protein OMA1 Zinc Metallopeptidase (OMA1) in a sample obtained from the subject;
comparing the expression level of protein OMA1 in the sample with a protein OMA1 reference expression level, wherein the subject is diagnosed as having metastatic breast cancer when the expression level of protein OMA1 in the sample is less than the protein OMA1 reference expression level; and
administering a therapy to the diagnosed subject, the therapy being a chemotherapeutic agent.

9. The method of claim 8, wherein the chemotherapeutic agent is doxorubicin.

10. The method of claim 1, wherein the imaging device is selected from a device for phase imaging, fluorescent imaging, actin staining, BrdU staining, mitochondrial imaging, northern blotting, enzyme-linked immunoassay (ELISA), and Western blotting.

* * * * *